(12) United States Patent
Adams et al.

(10) Patent No.: US 8,574,219 B2
(45) Date of Patent: Nov. 5, 2013

(54) CATHETER SHAFT INCLUDING A METALLIC TAPERED REGION

(75) Inventors: Mark L. Adams, Sandy, UT (US); Todd Beaupre, Reading, MA (US); Christopher Nardone, N. Chelmsford, MA (US); Mark Girard, Medway, MA (US); Raymond Lareau, Westford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1357 days.

(21) Appl. No.: 11/522,561

(22) Filed: Sep. 18, 2006

(65) Prior Publication Data

US 2008/0097395 A1 Apr. 24, 2008

(51) Int. Cl.
*A61M 25/00* (2006.01)

(52) U.S. Cl.
USPC ........................................................ 604/525

(58) Field of Classification Search
USPC .................................... 604/525–527, 523
See application file for complete search history.

(56) References Cited

U.S. PATENT DOCUMENTS

| | | | |
|---|---|---|---|
| 4,964,409 A * | 10/1990 | Tremulis | 600/434 |
| 5,163,903 A | 11/1992 | Crittenden | |
| 5,275,152 A * | 1/1994 | Krauter et al. | 604/527 |
| 5,395,334 A | 3/1995 | Keith | |
| 5,484,425 A | 1/1996 | Fischell et al. | |
| 5,533,968 A | 7/1996 | Muni | |
| 5,662,622 A * | 9/1997 | Gore et al. | 604/526 |
| 5,718,683 A | 2/1998 | Ressemann | |
| 5,720,724 A | 2/1998 | Ressemann | |
| 5,772,642 A | 6/1998 | Ciamacco, Jr. | |
| 5,823,995 A | 10/1998 | Fitzmaurice | |
| 5,830,155 A * | 11/1998 | Frechette et al. | 604/526 |
| 5,921,958 A | 7/1999 | Ressemann | |
| 5,997,562 A * | 12/1999 | Zadno-Azizi et al. | 606/194 |
| 6,017,319 A | 1/2000 | Jacobsen | |
| 6,027,475 A | 2/2000 | Sirhan | |
| 6,102,890 A | 8/2000 | Stivland | |
| 6,428,489 B1 | 8/2002 | Jacobsen | |
| 6,579,246 B2 | 6/2003 | Jacobsen | |
| 6,712,807 B2 | 3/2004 | Stivland | |
| 7,540,865 B2 * | 6/2009 | Griffin et al. | 604/524 |
| 7,850,623 B2 * | 12/2010 | Griffin et al. | 600/585 |
| 8,231,551 B2 * | 7/2012 | Griffin et al. | 600/585 |
| 2004/0167437 A1 | 8/2004 | Sharrow | |
| 2004/0193140 A1 * | 9/2004 | Griffin et al. | 604/524 |
| 2006/0190024 A1 | 8/2006 | Bei et al. | |
| 2007/0100285 A1 * | 5/2007 | Griffin et al. | 604/164.11 |
| 2010/0256601 A1 * | 10/2010 | Lippert et al. | 604/523 |

FOREIGN PATENT DOCUMENTS

| | | |
|---|---|---|
| WO | 99/11313 A1 | 3/1999 |
| WO | 03/000116 A2 | 1/2003 |

* cited by examiner

*Primary Examiner* — Kevin C Sirmons
*Assistant Examiner* — Andrew Gilbert
(74) *Attorney, Agent, or Firm* — Seager, Tufte & Wickhem, LLC (57) ABSTRACT

A catheter shaft including a metallic tubular member including a plurality of apertures formed in the tubular wall of the metallic tubular member to provide a desired degree of flexibility to the metallic tubular member. The metallic tubular member includes a tapered region intermediate a region and a second, reduced diameter region relative to the first region.

23 Claims, 7 Drawing Sheets

CATHETER SHAFT INCLUDING A METALLIC TAPERED REGION

TECHNICAL FIELD

The invention relates generally to medical devices. More specifically, the invention pertains to a medical device, such as a catheter or the like, including a metallic tapered region.

BACKGROUND

Elongate medical devices are commonly used to facilitate navigation through and/or treatment within the anatomy of a patient. A variety of elongate medical devices for intracorporeal use, such as catheters, guidewires, endoscopes, and the like have been developed over the past several decades. Because the anatomy of a patient may be very tortuous, it is often desirable to combine a number of performance features in such devices. For example, it is sometimes desirable to combine characteristics such as pushability and torqueability with characteristics such as flexibility. A number of different elongated medical device structures and assemblies are known, each having certain advantages and disadvantages. However, there is an ongoing need to provide alternative elongated medical device structures, assemblies, and methods. For example, a number of different shaft structures, assemblies, and methods for medical devices are known, but there is an ongoing need to provide alternatives to those that are known.

SUMMARY

The disclosure is directed to a medical device including a shaft having a metallic tapered region, and a method of manufacturing the same.

Accordingly, one embodiment illustrates a catheter shaft including a metallic shaft having a distal region and a reduced diameter proximal region relative to the distal region. The metallic shaft includes a tapered region intermediate the distal region and the reduced diameter proximal region.

Another embodiment illustrates a catheter shaft including a metallic shaft having a distal region having an outer diameter and a proximal region having an outer diameter, wherein the outer diameter of the distal region is greater than the outer diameter of the proximal region of the metallic shaft. A polymeric material may extend over at least a portion of the proximal region of the metallic shaft.

Another embodiment illustrates a catheter including a hub assembly and an elongate shaft coupled to the hub assembly. The elongate shaft includes a metallic tubular member having a distal region and a reduced diameter proximal region having an outer diameter less than the outer diameter of the distal region. The metallic tubular member may include a tapered region intermediate the proximal region and the distal region. At least a portion of the metallic tubular member may include a plurality of apertures formed therein to provide the elongate shaft with a desired degree of lateral flexibility. A polymeric member may overlay at least a portion of the proximal region of the metallic tubular member.

BRIEF DESCRIPTION OF THE DRAWINGS

The invention may be more completely understood in consideration of the following detailed description of various embodiments in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

Detailed Description

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 1:
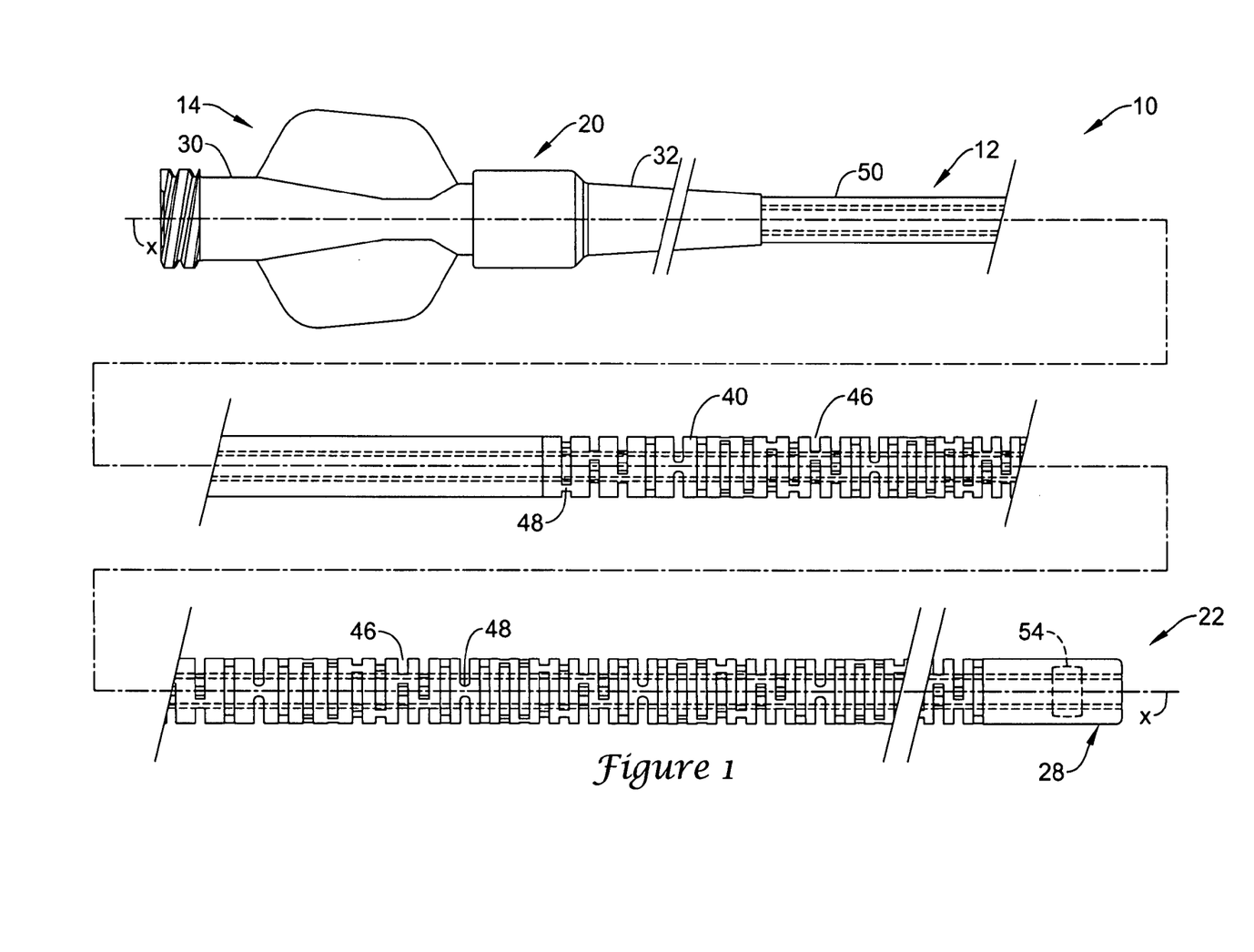
FIG. 1 is a plan view of an exemplary embodiment of a medical catheter.
Figure 2:
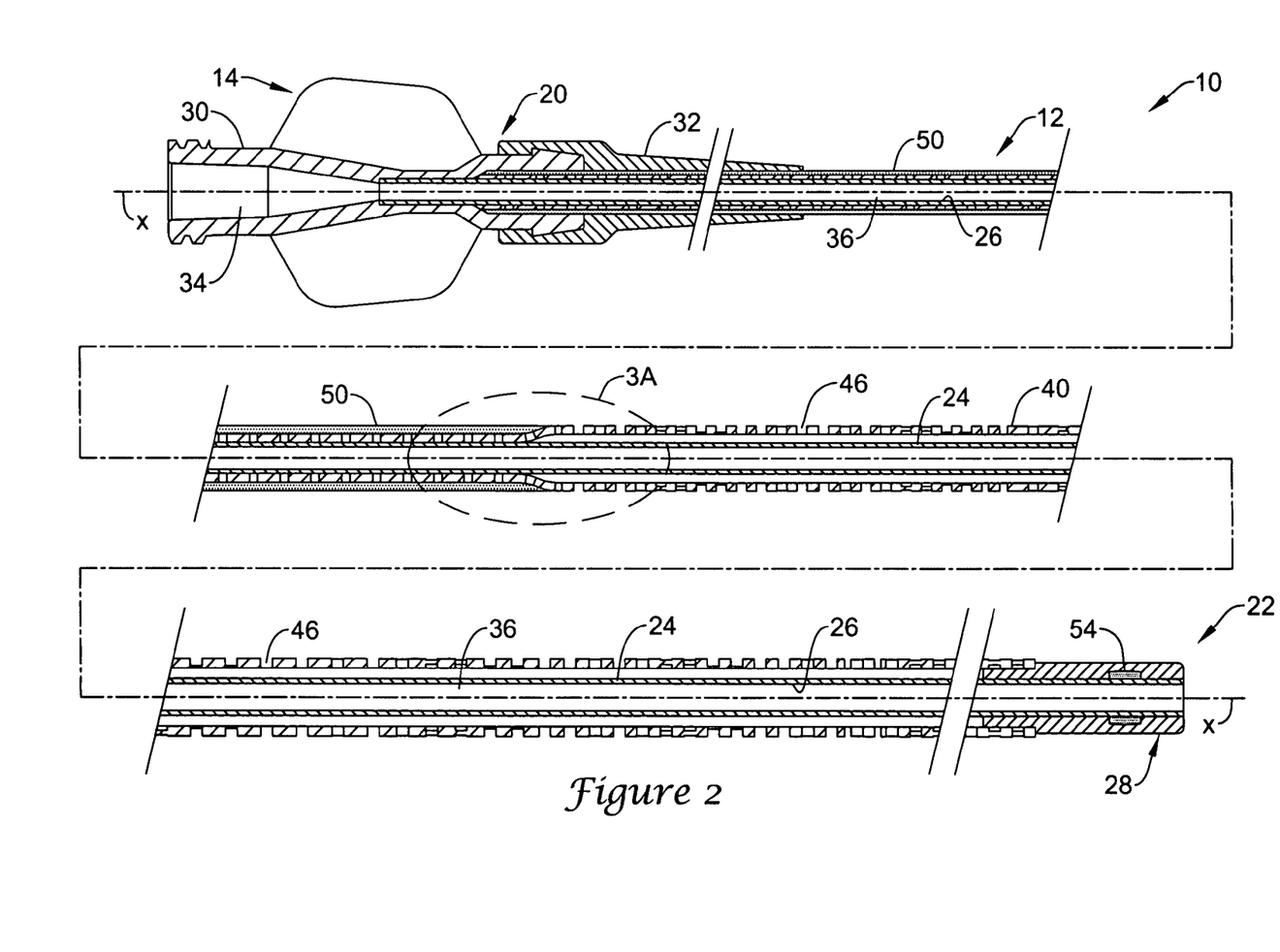
FIG. 2 is a cross-sectional view of the medical catheter of FIG. 1.

An elongate medical device, illustrated as a catheter 10, is shown in FIG. 1. The catheter 10 includes an elongate shaft 12 extending from a proximal end 20 to a distal end 22. A manifold assembly 14 is coupled to the proximal end 20 of the elongate shaft 12. The manifold assembly 14 may include a hub 30 and/or a strain relief 32. As shown in FIG. 2, the hub 30 may include a bore 34 in fluid communication with a lumen of the elongate shaft 12. The distal end 22 of the elongate shaft 12 includes a distal tip 28.

The elongate shaft 12 can be manufactured, include structure, and be made of materials so as to provide the desired characteristics of the catheter 10, depending upon the intended use. For example, the elongate shaft 12 can be provided with and/or manufactured so as to maintain a desired level of flexibility, torqueability and/or other characteristics appropriate for maneuvering the catheter 10 as desired, for example, through the vasculature of a patient.

The elongate shaft 12 may have a length and an outside diameter appropriate for its desired use, for example, to enable intravascular insertion and navigation. For instance, in some embodiments, the elongate shaft 12 may have a length in the range of about 1 to about 300 centimeters or more, or in some embodiments, in the range of about 20 cm to about 250 cm, and an outside diameter in the range of about 1 F (French) to about 20 F, or in some embodiments, in the range of about 1 F to about 10 F. Additionally, although depicted as including a generally round outer diameter and a round cross-sectional shape, it can be appreciated that the elongate shaft 12 can include other outer diameter and/or cross-sectional shapes or combinations of shapes without departing from the spirit of the invention. For example, the outer diameter and/or cross-sectional shape of the generally tubular shaft 12 may be oval, rectangular, square, triangular, polygonal, and the like, or combinations thereof, or any other suitable shape, depending upon the desired characteristics.

In some embodiments, the catheter 10 can be a microcatheter including an elongate shaft 12 that is adapted and/or configured for use within small anatomies of a patient. For example, some embodiments are particularly useful in treating targets located in tortuous and/or narrow vessels. Some examples of such vessels may include those in the neurovascular system, in certain sites within the coronary vascular system, or in sites within the peripheral vascular system such as superficial femoral, popliteal, or renal arteries. The target site in some embodiments is a neurovascular site, such as a site in the brain which is accessible only via a tortuous vascular path, for example, a vascular path containing a plurality of bends or turns which may be greater than about 90°, and/or involving vessels which are in the range of about 8 mm or less, and in some cases as small as about 2-3 mm or less, in diameter. As such, in some embodiments, the elongate shaft 12 can include an outside diameter in the range of approximately 1 F-4 F.

However, in other embodiments, the catheter 10 may be used in other target sites within the anatomy of a patient, in which case the elongate shaft 12 would be so adapted. For example, the catheter 10 may be suited for other uses in the digestive system, soft tissues, or any other use including insertion into an organ for medical uses, and the elongate shaft 12 could be appropriately adapted for such uses. For example, in some embodiments, the catheter 10 may be used as an introducer sheath, in which case the elongate shaft 12 may be significantly shorter. The catheter 10 may also include additional structure and materials adapted for a particular use and/or procedure. For example, in some other embodiments, the elongate shaft 12 may include additional devices or structures such as inflation or anchoring members, device deployment members, sensors, optical elements, ablation devices, or the like, or any of a broad variety of other structures depending upon the desired function and characteristics of the catheter 10.

In at least some embodiments, the elongate shaft 12 can have a generally tubular construction that includes at least one lumen extending the length of the elongate shaft 12 along the longitudinal axis x. This can also be seen with reference to FIG. 3A, which is an enlarged cross-sectional view of a portion of the shaft 12 including a transition region of the elongate shaft 12.

In the illustrative embodiment, the elongate shaft 12 includes a metallic tubular member 40. The metallic tubular member 40 may be formed of any desired material. Some examples of suitable metals and metal alloys can include stainless steel, such as 304V, 304L, and 316L stainless steel; nickel-titanium alloy such as a superelastic (i.e., pseudoelastic) or linear elastic nitinol; nickel-chromium alloy; nickel-chromium-iron alloy; cobalt alloy; tungsten or tungsten alloys; tantalum or tantalum alloys, gold or gold alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); or the like; or other suitable metals, or combinations or alloys thereof. In some embodiments, it is desirable to use metals or metal alloys that are suitable for metal joining techniques such as welding, soldering, brazing, crimping, friction fitting, adhesive bonding, etc.

The metallic tubular member 40 may include a plurality of apertures 46, such as grooves, cuts, slits, slots, or the like, processed in the wall of the metallic tubular member 40. The apertures 46 may be processed in a portion of, or along the entire length of, the metallic tubular member 40. Such a structure may be desirable because it may allow the metallic tubular member 40, or select portions thereof, to have a desired level of lateral flexibility as well as have the ability to transmit torque and pushing forces through the metallic tubular member 40. The apertures 46 may be formed in essentially any known way. For example, the apertures 46 can be formed by methods such as micro-machining, saw-cutting, laser cutting, grinding, milling, casting, molding, chemically etching or treating, or other known methods, and the like. In some such embodiments, the structure of the metallic tubular member 40 is formed by cutting and/or removing portions of the metallic tubular member 40 to form the apertures 46. Some such metallic tubular members 40 are commonly referred to as hypotubes.

In some embodiments, the apertures 46 can extend entirely through the wall of the metallic tubular member 40, or the apertures 46 can extend only partially into the wall of the metallic tubular member 40. Other embodiments may include combinations of both complete and partial apertures 46 through the wall of the metallic tubular member 40. Additionally, the quantity, size, spacing, distribution, and/or orientation of the apertures 46 can be varied to achieve desired characteristics. For example, the quantity or density of the apertures 46 along the length of the metallic tubular member 40 may be constant or may vary, depending upon desired characteristics. For example, the density of the apertures 46 in a distal portion of the metallic tubular member 40 may be greater than the density of the apertures 46 in a proximal portion of the metallic tubular member 40. In such embodiments, the flexibility of a distal portion of the elongate shaft 12 may be greater than the flexibility of a proximal portion of the elongate shaft 12. In other embodiments, alternative regions of the metallic tubular member 40 may have different degrees of flexibility resultant of the chosen size, spacing, distribution, and/or orientation of the apertures 46. One of skill in the art would recognize that other arrangements of the apertures 46 may be imparted in the metallic tubular member 40 to achieve desired characteristics.

As shown in FIG. 1, the apertures 46 may be formed such that one or more spines or beams 48 are formed in the metallic tubular member 40. Such spines or beams 48 could include portions of the metallic tubular member 40 that remain after the apertures 46 are formed in the body of the metallic tubular member 40. Such spines or beams 48 may act to maintain a relatively high degree of torsional stiffness while maintaining a desired level of lateral flexibility. In some embodiments, some adjacent apertures 46 can be formed such that they include portions that overlap with each other about the circumference of the metallic tubular member 40. In other embodiments, some adjacent apertures 46 can be disposed such that they do not necessarily overlap with each other, but are disposed in a pattern that provides the desired degree of lateral flexibility. Additionally, the apertures 46 can be arranged along the length of, or about the circumference of, the metallic tubular member 40 to achieve desired properties. For example, the apertures 46 can be arranged in a symmetrical pattern, such as being disposed essentially equally on opposite sides about the circumference of the metallic tubular member 40, or equally spaced along the length of the metallic tubular member 40, the apertures 46 can be arranged in an increasing or decreasing density pattern, or the apertures 46 can be arranged in a non-symmetric or irregular pattern.

Some additional examples of shaft constructions and/or arrangements of cuts or slots formed in a tubular member are disclosed in U.S. Pat. Nos. 6,428,489 and 6,579,246, which are each incorporated herein by reference. Additionally, U.S. Publication No. 2004/0193140, which is incorporated herein by reference, illustrates additional arrangements of apertures providing a degree of lateral flexibility formed in a medical device. The metallic tubular member 40 will further be described while referring to FIG. 3A.

The elongate shaft 12 may also include a polymeric member 50 extending distally of the manifold assembly 14 and overlaying a proximal portion of the metallic tubular member 40. In some embodiments, the polymeric member 50 may be extruded over the metallic tubular member 40, the polymeric member 50 may be molded onto the metallic tubular member 40, or the polymeric member 50 may be heat shrunk onto the metallic tubular member 40. In other embodiments, the polymeric member 50 may be positioned over a portion of the metallic tubular member 40 in other fashions known in the art. The polymeric member 50 may include any of a variety of suitable polymer materials, and in some embodiments, the polymeric member 50 may include a reinforcing member such as a braid or a coil member. For instance, in some embodiments the polymeric member 50 may include polyamide, polyether block amide (PEBAX), polytetrafluoroethylene (PTFE), or the like. The polymeric member 50 will further be described while referring to FIG. 3A.

In some embodiments, such as the embodiment illustrated in FIG. 2, the elongate shaft 12 may also include an inner tubular member 24 disposed within the lumen of the metallic tubular member 40. The inner tubular member 24 may extend substantially the entire length of the elongate shaft 12, or a portion thereof. In some embodiments, such as the illustrative embodiment shown in FIG. 2, the inner tubular member 24 may have a relatively constant diameter along substantially the entire length of the inner tubular member 24. However, in other embodiments, the diameter of the inner tubular member 24 may vary in and/or along different regions of the catheter 10.

The inner tubular member 24 may include and/or be made of any of a broad variety of materials and/or structures. The inner tubular member 24 may have a single-layer tubular construction or a multi-layer tubular construction, or a combination thereof. For example, the inner tubular member 24 may be a single tubular member formed by a single layer of material, or in other embodiments, may be formed by a plurality of tubular members and/or a plurality of layers of material that may be the same and/or different, but in combination form the inner tubular member 24. In yet other embodiments, some portions of the inner tubular member 24 can include a single layer construction, while other portions may include a multi-layer construction. Some examples of suitable materials can include, but are not limited to, polymers, metals, metal alloys, or composites or combinations thereof.

Some examples of some suitable polymers can include, but are not limited to, polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyetherether ketone (PEEK), polyimide, polyamide, polyphenylene sulfide (PPS), polyphenylene oxide (PPO), polysufone, nylon, perfluoro(propyl vinyl ether) (PFA), polyether-ester, some adhesive resin such as modified polyolefin resin, polymer/metal composites, etc., or mixtures, blends or combinations thereof, and may also include or be made up of a lubricous polymer. Some other potentially suitable polymer materials may include those listed herein with reference to other components of the catheter 10. One example of a suitable polyether block ester is available under the trade name ARNITEL, and one suitable example of a polyether block amide (PEBA) is available under the trade name PEBAX®, from Atomchem Polymers, Birdsboro, Pa. In some embodiments, adhesive resins may be used, for example, as tie layers and/or as the material of the structures. One example of a suitable adhesive resin is a modified polyolefin resin available under the trade name ADMER®, from Mitsui Chemicals America, Inc. Additionally, polymer material can, in some instances, be blended with a liquid crystal polymer (LCP). For example, in some embodiments, the mixture can contain up to about 5% LCP. This has been found in some embodiments to enhance torqueability.

As shown in the illustrative embodiment, the distal end 22 of the shaft 12 can include a distal tip 28. The distal tip 28 can be a structure, assembly, construction and/or arrangement adapted and/or configured to provide characteristics such as shapability, flexibility, steerability, atraumatic characteristics, or the like, for example, to the distal portion and/or distal end of the shaft 12. A broad variety of distal tip constructions, configurations, and/or structures are generally known for use on medical devices, such as catheters, and may be used. In some embodiments, the distal tip 28 may be disposed at the distal end 22 of the shaft 12, and may extend distally beyond other portions of the shaft 12.

In some embodiments, the distal tip 28 is simply portions of the shaft 12, and/or components thereof that include materials and/or structures to provide the desired characteristics. For example, in the embodiment shown in FIG. 2, the distal tip 28 can include and/or extend about the distal portion of an inner tubular member 24 extending through the metallic tubular member 40. In this regard, the distal tip 28 may include the distal portion of the inner tubular member 24, and may additionally include one or more additional layers and/or structures disposed about the distal portion of the inner tubular member 24. In other embodiments, however, the distal tip 28 may include structure and/or material that may be considered to be separate and distinct from other portions of the shaft 12, but that is connected to the distal portion of the shaft 12 to form the distal tip 28.

Referring to FIG. 2, the elongate shaft 12 includes a lumen 36 extending therethrough. The lumen 36 is in fluid communication with a bore 34 of the hub 30. In the illustrative embodiment, the lumen 36 is defined by an inner surface 26 of the inner tubular member 24, and can have an inner diameter capable of transmitting fluids, or in some cases, receiving another medical device, such as a guidewire, a stent, a coil (such as an embolic coil, or the like), treatment particles (such as embolic particles, or the like), an ablation device, or another catheter, for example, a diagnostic catheter, a balloon catheter, a stent delivery catheter, or the like, or others. In some embodiments, the lumen 36 can be adapted and/or configured to accommodate another medical device having an outer diameter in the range of about 1 F to about 10 F.

In other embodiments not including an inner tubular member disposed within the metallic tubular member 40, a lumen may be defined by an inner surface of the metallic tubular member 40 having a diameter capable of receiving other medical devices therethrough.

The elongate shaft 12 may include one or more radiopaque markers 54 including a radiopaque material imparting a degree of radiopacity to the elongate shaft 12. In the illustrative embodiment, a radiopaque marker 54 is located within the distal tip 28 of the elongate shaft 12. However, in other embodiments, the one or more radiopaque markers 54 may be located at another location along the length of the elongate shaft 12. In other embodiments, all or portions of the elongate shaft 12 may be made of, impregnated with, plated or clad with, or otherwise include a radiopaque material and/or structure to facilitate radiographic visualization. Radiopaque materials are understood to be materials capable of producing a relatively bright image on a fluoroscopy screen or another imaging technique during a medical procedure. Some examples of radiopaque materials can include, but are not limited to, gold, platinum, palladium, tantalum, tungsten alloy, polymer material loaded with radiopaque filler, and the like.

Figure 3A:
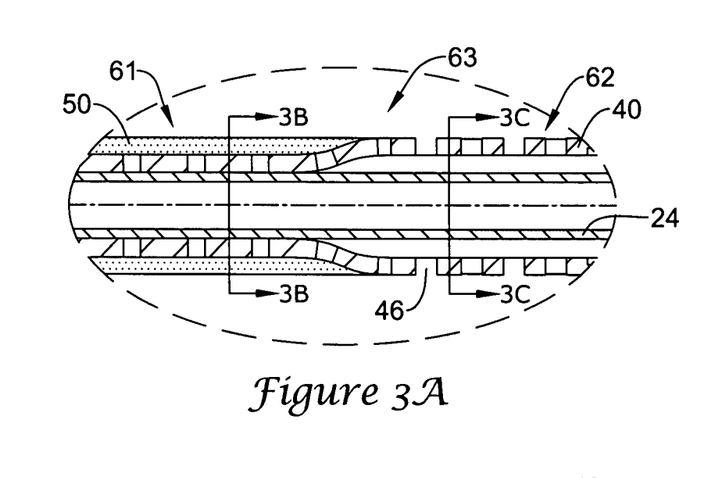
FIG. 3A is an enlarged cross-sectional view of a portion of the medical catheter of FIG. 2.

Referring now to FIG. 3A, the metallic tubular member 40 includes a first, or proximal region 61 and a second, or distal region 62. In describing the first and second regions 61, 62 the terms "proximal" and "distal" are intended to describe the relative spatial relationship between the first and second regions 61, 62. The proximal region 61 may be a generally cylindrical region and the distal region 62 may be a generally cylindrical region. The proximal region 61 has an outer diameter and the distal region 62 has an outer diameter greater than the outer diameter of the proximal region 61. Thus, the proximal region 61 may be considered to be a reduced diameter region relative to the distal region 62. A tapered region 63 may be intermediate the proximal region 61 and the distal region 62 to provide a transition between the outer diameter of the proximal region 61 and the outer diameter of the distal region 62.

The metallic tubular member 40 including the reduced diameter proximal region 61 and the distal region 62 may be continuously formed during an extrusion process. For instance, the distal region 62 may be extruded, and the reduced diameter proximal region 61 may be extruded during a drawdown extrusion process. A drawdown extrusion process is a process of pulling the extrudate away from an extrusion die at a linear speed higher than that at which the molten material is emerging from the die, thus reducing the cross-sectional dimensions of the extrudate. Thus, the reduced diameter proximal region 61 may be formed continuously with the distal region 62 of the metallic tubular member 40. It is noted that other processes may be utilized to form the metallic tubular member 40, or portions thereof. For example, a grinding process such as a centerless grinding process, a milling process, a machining process, molding, casting, or another process may be utilized in forming the metallic tubular member 40 having a reduced diameter portion relative to another portion of the metallic tubular member 40 and a tapered region or a stepped-down region therebetween.

The distal region 62 may include a plurality of apertures 46 formed therein to provide a degree of flexibility to the distal region 62 of the metallic tubular member 40. The proximal region 61 may additionally include a plurality of apertures 46 formed therein to provide a degree of flexibility to the proximal region 61 of the metallic tubular member 40. However, in some embodiments, the proximal region 61, or a portion thereof, may be devoid of any apertures 46 formed therein. The density of the apertures 46 in the distal region 62 may be different from the density of the apertures 46 in the proximal region 61. For instance, the density of apertures 46 in the distal region 62 may be greater than or less than the density of apertures 46 in the proximal region 61. The number, size, distribution and/or orientation of the apertures 46 may be otherwise varied along the length of the metallic tubular member 40 to impart desired flexibility properties and/or regions of the elongate shaft 12.

The polymeric member 50 may be located about the outer surface of the reduced diameter proximal region 61 of the metallic tubular member 40. Thus, the polymeric member 50 may overlay at least a portion of the reduced diameter proximal region 61 of the metallic tubular member 40. For example, the polymeric member 50 may extend from the tapered region 63 proximate the distal region 62 of the metallic tubular member 40 to a location proximate the proximal end of the metallic tubular member 40. The polymeric member 50 may be sized such that the outer diameter of the polymeric member 50 is substantially similar to the outer diameter of the distal region 62 of the metallic tubular member 40. However in other embodiments, the outer diameter of the polymeric member 50 and the outer diameter of the distal region 62 of the metallic tubular member 40 may be dissimilar, thus creating a transition in the outer diameter of the elongate shaft 12 at the transition between the polymeric member 50 and the metallic tubular member 40. In other embodiments, the polymeric member 50, or another polymeric member, may be disposed about at least a portion of the distal region 62 as well.

In some embodiments, the distal region 62 of the metallic tubular member 40 may have an outer diameter of about 0.89 mm (0.035 in), and the proximal region 61 may have an outer diameter of about 0.635 mm (0.025 in). The inner diameter of the distal region 62 may be in the range of about 0.38 mm to about 0.635 mm (0.015 in-0.025 in), and the inner diameter of the proximal region 61 may be less than the inner diameter of the distal region 62 as a result of manufacturing the metallic tubular member 40. The polymeric member 50 may have an outer diameter of about 0.89 mm (0.035 in), giving the outer diameter of the elongate shaft 12 uniformity along its length. Although some suitable dimensions are disclosed, one of skill in the art would understand that the elongate shaft 12 may include dimensions which deviate from those expressly disclosed.

In the illustrative embodiment, a proximal portion of the elongate shaft 12, including a portion of the reduced diameter proximal region 61, a portion of the inner tubular member 24, and a portion of the polymeric member 50, extends into the manifold assembly 14. The elongate shaft 12 may be coupled to the manifold assembly 14 in any known way. For example, the elongate shaft 12 may be secured to the manifold assembly 14 by thermal bonding such as laser bonding, chemical bonding, adhesive bonding, welding such as RF welding, mechanical means, or the like. As shown in FIG. 2, the inner tubular member 24 extends proximally beyond the metallic tubular member 40, thus the inner tubular member 24 may be secured directly to the manifold assembly 14.

The polymeric member 50 extends distally from the strain relief 32 of the manifold assembly 14 for a desired length. In some embodiments, the polymeric member 50 may terminate at a location proximal of the distal end of the metallic tubular member 40. For example, in some embodiments, the polymeric member 50 may extend in a range of about 15 cm (6 in) to about 150 cm (60 in) distally beyond the strain relief 32. For example, the reduced diameter proximal region 61 may extend about 15 cm (6 in), 30 cm (12 in), 50 cm (20 in), 100 cm (40 in) or 150 cm (60 in), thus, the reduced diameter proximal region 61 may extend in the range of about 15 cm (6 in) to about 150 cm (60 in) and the polymeric member 50 may overlay a portion of, a majority of, or substantially the entire length of the proximal region 61. However, in other embodiments, the reduced diameter proximal region 61 may be less than 15 cm (6 in). In yet other embodiments, the reduced diameter proximal region 61 may be greater than 150 cm (60 in). Although some suitable dimensions are disclosed, one of skill in the art would understand that desired dimensions may deviate from those expressly disclosed. The combination of the reduced diameter proximal region 61 of the metallic tubular member 40 and the polymeric member 50 overlaying the proximal region 61 may provide pressure strength and/or flexibility to a proximal portion of the catheter 10.

Figure 3B:
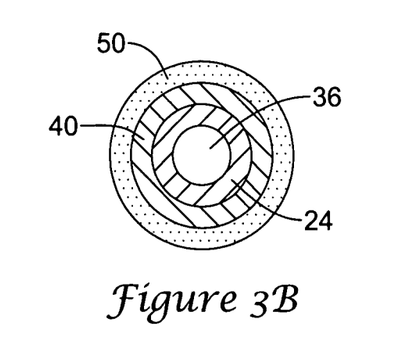
FIG. 3B is a cross-sectional view of the catheter shaft taken along line 3B-3B of FIG. 3A.

FIG. 3B is a cross-sectional view of the elongate shaft 12 taken along line 3B-3B of FIG. 3A. In the proximal region 61, the metallic tubular member 40 may be interposed between the inner tubular member 24 and the polymeric member 50, such that the inner surface of the metallic tubular member 40 is contiguous with the inner tubular member 24 and the outer surface of the metallic tubular member 40 is contiguous with the polymeric member 50. However, in some embodiments, the metallic tubular member 40 may be spaced away from one or both of the inner tubular member 24 and the polymeric member 50 and/or another layer of material may be interposed between the metallic tubular member 40 and the polymeric member 50.

Figure 3C:
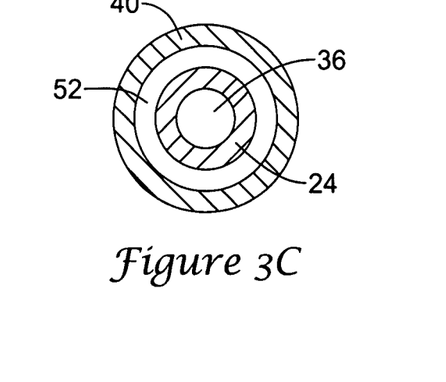
FIG. 3C is a cross-sectional view of the catheter shaft taken along line 3C-3C of FIG. 3A.

FIG. 3C is a cross-sectional view of the elongate shaft 12 taken along line 3C-3C of FIG. 3A. In the distal region 62, the inner tubular member 24, which may be coaxially disposed within the lumen of the metallic tubular member 40, may be spaced away from the metallic tubular member 40, creating a gap 52 therebetween. In such an embodiment, the inner tubular member 24 may maintain a constant diameter throughout the length of the elongate shaft 12. In the distal region 62, the inner tubular member 24 may be secured to the metallic tubular member 40 at one or a plurality of discrete attachment points proximate the distal end of the elongate shaft 12 and/or along the length of the distal region 62.

Figure 4:
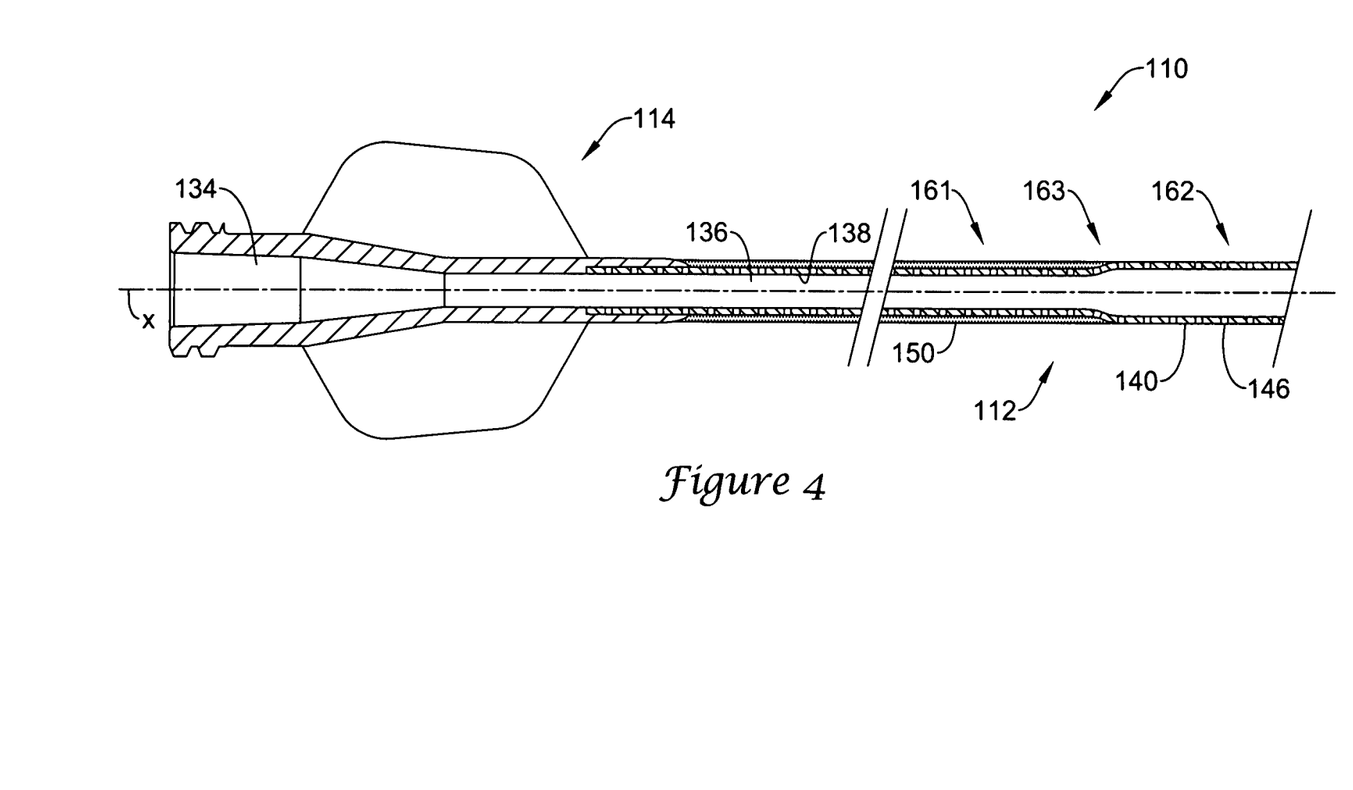
FIG. 4 is an enlarged cross-sectional view of an alternative embodiment of a medical catheter.

An alternative embodiment of a portion of a catheter 110 is illustrated in FIG. 4. The catheter 110 includes an elongate shaft 112 and a manifold assembly 114 coupled to the elongate shaft 112. The elongate shaft 112 includes a metallic tubular member 140 and a polymeric member 150 overlaying at least a portion of the metallic tubular member 140.

The metallic tubular member 140 includes a first, or proximal region 161 and a second, or distal region 162. In describing the first and second regions 161, 162 the terms "proximal" and "distal" are intended to describe the relative spatial relationship between the first and second regions 161, 162. The proximal region 161 may be a generally cylindrical region and the distal region 162 may be a generally cylindrical region. The proximal region 161 has an outer diameter and the distal region 162 has an outer diameter greater than the outer diameter of the proximal region 161. Thus, the proximal region 161 may be considered to be a reduced diameter region relative to the distal region 162. A tapered region 163 may be intermediate the proximal region 161 and the distal region 162 to provide a transition between the outer diameter of the proximal region 161 and the outer diameter of the distal region 162. In some embodiments, the metallic tubular member 140 may be formed during an extrusion process including a drawdown extrusion process. In many respects, the metallic tubular member 140 may be similar to the metallic tubular member 40 discussed above regarding FIG. 3A. Thus, for the sake of repetitiveness, similarities of the metallic tubular member 140 with the metallic tubular member 40 will not be repeated. For example, the metallic tubular member 140 may include a plurality of apertures 146 formed therein to provide a degree of flexibility to the elongate shaft 112. Thus, the proximal region 161 and/or the distal region 162 may include apertures 146 formed therein.

As shown in FIG. 4, a proximal portion of the proximal region 161 may extend into the manifold assembly 114. Therefore, the lumen 136 of the elongate shaft 112, defined by the inner surface 138 of the metallic tubular member 140, may be in fluid communication with the bore 134 of the manifold assembly 114. Thus in some embodiments, the lumen 136 may be capable of receiving another medical device, or in some cases, transmitting fluids therethrough.

The polymeric member 150 may be disposed over a portion of the metallic tubular member 140 between the manifold assembly 114 and the tapered region 163 proximate the distal region 162. Thus, in some embodiments the polymeric member 150 may overlay a portion of, a majority of, or substantially the entire length of the proximal region 161 of the metallic tubular member 140. For instance, in some embodiments the polymeric member 150 and/or the metallic tubular member 140 may have dimensions similar to those expressed above regarding the polymeric member 50 and the metallic tubular member 40. The polymeric member 150 may have an outer diameter substantially similar to the outer diameter of the distal region 162, thus forming a uniform transition along the elongate shaft 112. However, in other embodiments, the outer diameter of the polymeric member 150 and the outer diameter of the distal region 162 of the metallic tubular member 140 may be dissimilar, thus creating a transition in the outer diameter of the elongate shaft 112 at the transition between the polymeric member 150 and the metallic tubular member 140. The combination of the reduced diameter proximal region 161 of the metallic tubular member 140 and the polymeric member 150 overlaying the proximal region 161 may provide pressure strength and/or flexibility to a proximal portion of the catheter 110. In other embodiments, the polymeric member 150, or another polymeric member, may be disposed about at least a portion of the distal region 162 as well.

The polymeric member 150 may include any suitable material and/or structure including, but not limited to, those disclosed above regarding the polymeric member 50. In some embodiments, the polymeric member 150 may be extruded over the metallic tubular member 140, the polymeric member 150 may be molded onto the metallic tubular member 140, or the polymeric member 150 may be heat shrunk onto the metallic tubular member 140. In other embodiments, the polymeric member 150 may be positioned over a portion of the metallic tubular member 140 in other fashions known in the art.

Figure 5A:
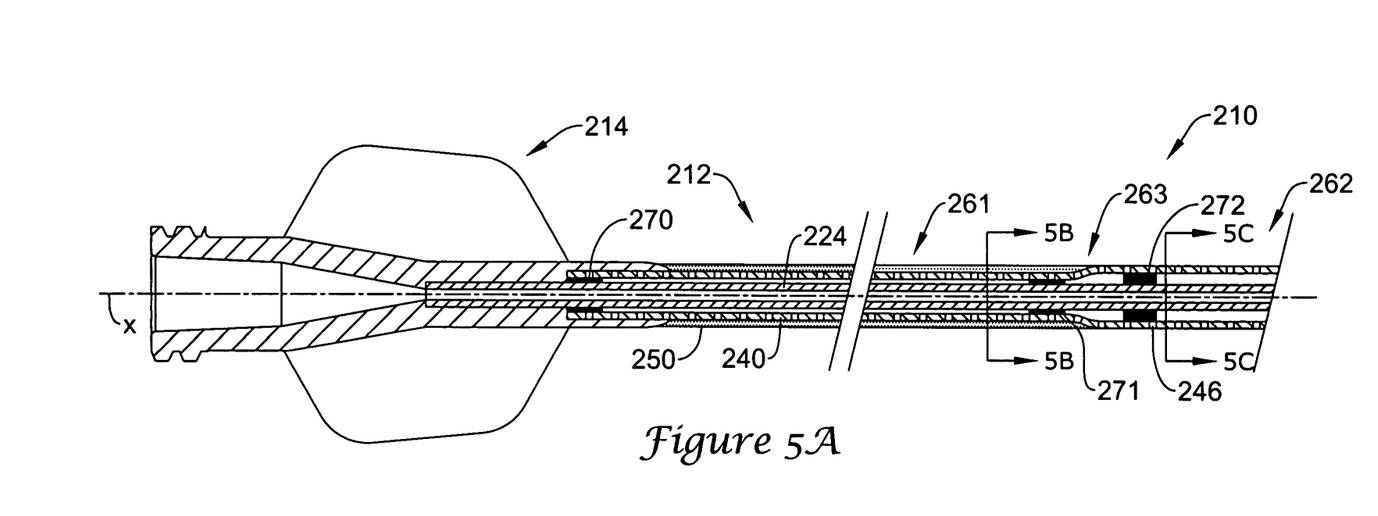
FIG. 5A is an enlarged cross-sectional view of an alternative embodiment of a medical catheter.

An alternative embodiment of a portion of a catheter 210 is illustrated in FIG. 5A. The catheter 210 includes an elongate shaft 212 and a manifold assembly 214 coupled to the elongate shaft 212. The elongate shaft 212 includes an inner tubular member 224, a metallic tubular member 240 and a polymeric member 250 overlaying at least a portion of the metallic tubular member 240.

The metallic tubular member 240 includes a first, or proximal region 261 and a second, or distal region 262. In describing the first and second regions 261, 262 the terms "proximal" and "distal" are intended to describe the relative spatial relationship between the first and second regions 261, 262. The proximal region 261 may be a generally cylindrical region and the distal region 262 may be a generally cylindrical region. The proximal region 261 has an outer diameter and the distal region 262 has an outer diameter greater than the outer diameter of the proximal region 261. Thus, the proximal region 261 may be considered to be a reduced diameter region relative to the distal region 262. A tapered region 263 may be intermediate the proximal region 261 and the distal region 262 to provide a transition between the outer diameter of the proximal region 261 and the outer diameter of the distal region 262. In some embodiments, the metallic tubular member 240 may be formed during an extrusion process including a drawdown extrusion process. In many respects, the metallic tubular member 240 may be similar to the metallic tubular member 40 discussed above regarding FIG. 3A. Thus, for the sake of repetitiveness, similarities of the metallic tubular member 240 with the metallic tubular member 40 will not be repeated. For example, the metallic tubular member 240 may include a plurality of apertures 246 formed therein to provide a degree of flexibility to the elongate shaft 212. Thus, the proximal region 261 and/or the distal region 262 may include apertures 246 formed therein.

In the illustrative embodiment, a proximal portion of the elongate shaft 212, including a portion of the reduced diameter proximal region 261 and a portion of the inner tubular member 224, extends into the manifold assembly 214. The elongate shaft 212 may be coupled to the manifold assembly 214 in any known way. For example, the elongate shaft 212 may be secured to the manifold assembly 214 by thermal bonding such as laser bonding, chemical bonding, adhesive bonding, welding such as RF welding, mechanical means, or the like. As shown in FIG. 5A, the inner tubular member 224 extends proximally beyond the metallic tubular member 240, thus the inner tubular member 224 may be secured directly to the manifold assembly 214.

The polymeric member 250 may be disposed over a portion of the metallic tubular member 240 between the manifold assembly 214 and the tapered region 263 proximate the distal region 262. Thus, in some embodiments the polymeric member 250 may overlay a portion of, a majority of, or substantially the entire length of the proximal region 261 of the metallic tubular member 240. For instance, in some embodiments the polymeric member 250 and/or the metallic tubular member 240 may have dimensions similar to those expressed above regarding the polymeric member 50 and the metallic tubular member 40. The polymeric member 250 may have an outer diameter substantially similar to the outer diameter of the distal region 262, thus forming a uniform transition along the elongate shaft 212. However in other embodiments, the outer diameter of the polymeric member 250 and the outer diameter of the distal region 262 of the metallic tubular member 240 may be dissimilar, thus creating a transition in the outer diameter of the elongate shaft 212 at the transition between the polymeric member 250 and the metallic tubular member 240. The combination of the reduced diameter proximal region 261 of the metallic tubular member 240 and the polymeric member 250 overlaying the proximal region 261 may provide pressure strength and/or flexibility to a proximal portion of the catheter 210. In other embodiments, the polymeric member 250, or another polymeric member, may be disposed about at least a portion of the distal region 262 as well.

The polymeric member 250 may include any suitable material and/or structure including, but not limited to, those disclosed above regarding the polymeric member 50. In some embodiments, the polymeric member 250 may be extruded over the metallic tubular member 240, the polymeric member 250 may be molded onto the metallic tubular member 240, or the polymeric member 250 may be heat shrunk onto the metallic tubular member 240. In other embodiments, the polymeric member 250 may be positioned over a portion of the metallic tubular member 240 in other fashions known in the art.

The inner tubular member 224 may be coupled to the metallic tubular member 240 at one or a plurality of discrete attachment points. For example, the inner tubular member 224 may be coupled to the proximal end of the metallic tubular member 240 at a discrete attachment point 270, the inner tubular member 224 may be coupled to the reduced diameter proximal region 261 of the metallic tubular member 240 proximate the tapered region 263 at a discrete attachment point 271, and/or the inner tubular member 224 may be coupled to the distal region 262 of the metallic tubular member 240 at a discrete attachment point 272. In some embodiments, such attachment points can be achieved using an adhesive material, for example, a cyanoacrylate, or other suitable type of adhesive. In at least some embodiments, only a relatively small portion of the metallic tubular member 240 is connected to the inner tubular member 224 at the attachment points. For example, the length of each individual bond joint, especially at intermediate bond joints, may be only about 5 cm or less, 3 cm or less, 1 cm or less, or 0.5 cm or less.

Figure 5B:
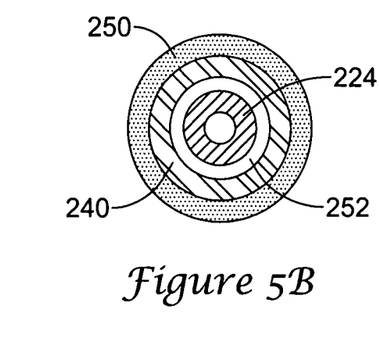
FIG. 5B is a cross-sectional view of the catheter of FIG. 5A taken along line 5B-5B.

FIG. 5B is a cross-sectional view of the elongate shaft 212 taken along line 5B-5B of FIG. 5A. In the proximal region 261, the metallic tubular member 240 may be coaxially disposed between the inner tubular member 224 and the polymeric member 250, such that the metallic tubular member 240 is spaced away from the inner tubular member 224, defining a gap 252 therebetween, and the outer surface of the metallic tubular member 240 is contiguous with the polymeric member 250. However, in some embodiments the metallic tubular member 240 may be contiguous with the inner tubular member 224 and/or spaced away from the polymeric member 250, and/or another layer of material may be interposed between the metallic tubular member 240 and the inner tubular ember 224 and/or the polymeric member 250. Discrete attachment points may be utilized in embodiments wherein the metallic tubular member 240 is spaced away from another tubular member in order to secure the metallic tubular member 240 to another tubular member.

Figure 5C:
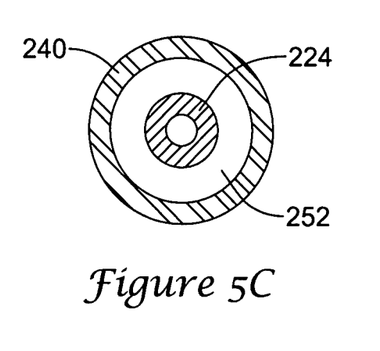
FIG. 5C is a cross-sectional view of the catheter of FIG. 5A taken along line 5C-5C.

FIG. 5C is a cross-sectional view of the elongate shaft 212 taken along line 5C-5C of FIG. 5A. In the distal region 262, the inner tubular member 224, which may be coaxially disposed within the lumen of the metallic tubular member 240 such that the inner tubular member 224 may be spaced away from the metallic tubular member 240, creating a gap 252 therebetween. In such an embodiment, the inner tubular member 224 may maintain a constant diameter throughout the length of the elongate shaft 212. As described above, in the distal region 262, the inner tubular member 224 may be secured to the metallic tubular member 240 at one or a plurality of discrete attachments points proximate the distal end of the elongate shaft 212 and/or along the length of the distal region 262.

One possible way of manufacturing the catheter 10, 110, 210 is forming an elongate shaft 12, 112, 212 by extruding a metallic tubular member 40, 140, 240 through an extrusion die. A drawdown extrusion process may be used to form the reduced diameter proximal region 61, 161, 261 of the metallic tubular member 40, 140, 240. Thus, the outer diameter of the proximal region 61, 161, 261 may be reduced relative to the distal region 62, 162, 262 during the drawdown process, forming a tapered region 63, 163, 263 intermediate the proximal region 61, 161, 261 and the distal region 62, 162, 262 which provides a transition between the dissimilar outer diameters of the metallic tubular member 40, 140, 240.

A polymeric member 50, 150, 250 may be disposed over at least a portion of the reduced diameter proximal region 61, 161, 261. In some embodiments, the polymeric member 50, 150, 250 may be extruded over the metallic tubular member 40, 140, 240, the polymeric member 50, 150, 250 may be molded onto the metallic tubular member 40, 140, 240, or the polymeric member 50, 150, 250 may be heat shrunk onto the metallic tubular member 40, 140, 240. In other embodiments, the polymeric member 50, 150, 250 may be positioned over a portion of the metallic tubular member 40, 140, 240 in other fashions known in the art.

In some embodiments the polymeric member 50, 150, 250 may be disposed on the proximal region 61, 161, 261 prior to coupling the elongate shaft 12, 112, 212 to a manifold assembly 14, 114, 214. However, in other embodiments, the polymeric member 50, 150, 250 may be disposed on the proximal region 61, 161, 261 subsequent to coupling the elongate shaft 12, 112, 212 to a manifold assembly 14, 114, 214.

The proximal end of the elongate shaft 12, 112, 212 may be coupled to a manifold assembly 14, 114, 214. Thus, the catheter 10, 110, 210 may include an elongate shaft 12, 112, 212 extending distally from a manifold assembly 14, 114, 214. The elongate shaft 12, 112, 212 includes a metallic tubular member 40, 140, 240 having a distal region 62, 162, 262 and a reduced diameter proximal region 61, 161, 261 relative to the distal region 62, 162, 262. A polymeric member 50, 150, 250 may extend distally from the manifold assembly 14, 114, 214 for at least a portion of the length of the reduced diameter proximal region 61, 161, 261. The combination of the reduced diameter proximal region 61, 161, 261 of the metallic tubular member 40, 140, 240 and the polymeric member 50, 150, 250 overlaying the proximal region 61, 161, 261 may provide pressure strength and/or flexibility to a proximal portion of the catheter 10, 110, 210.

Figure 6:
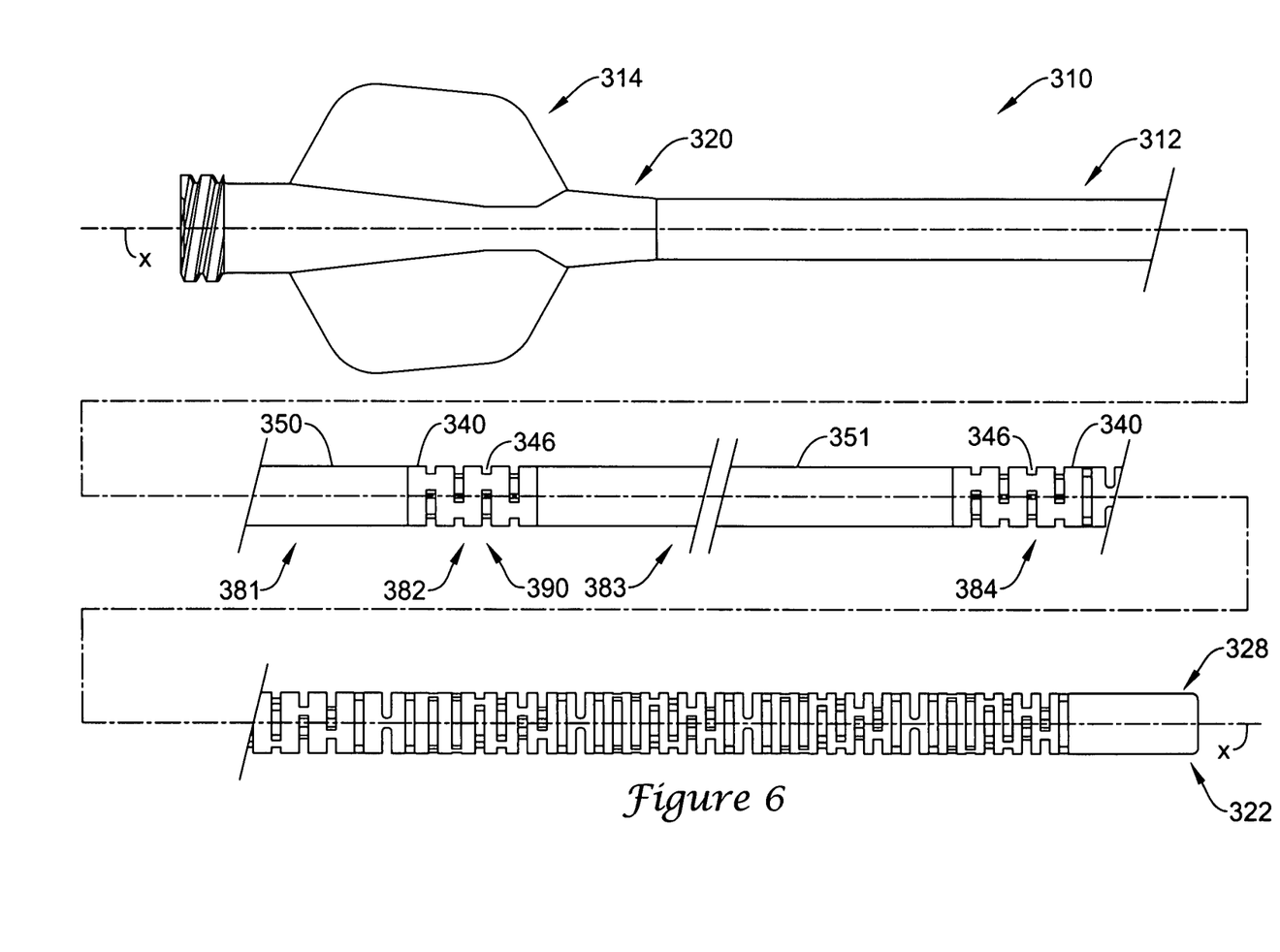
FIG. 6 is a plan view of another exemplary embodiment of a medical catheter.
Figure 7:
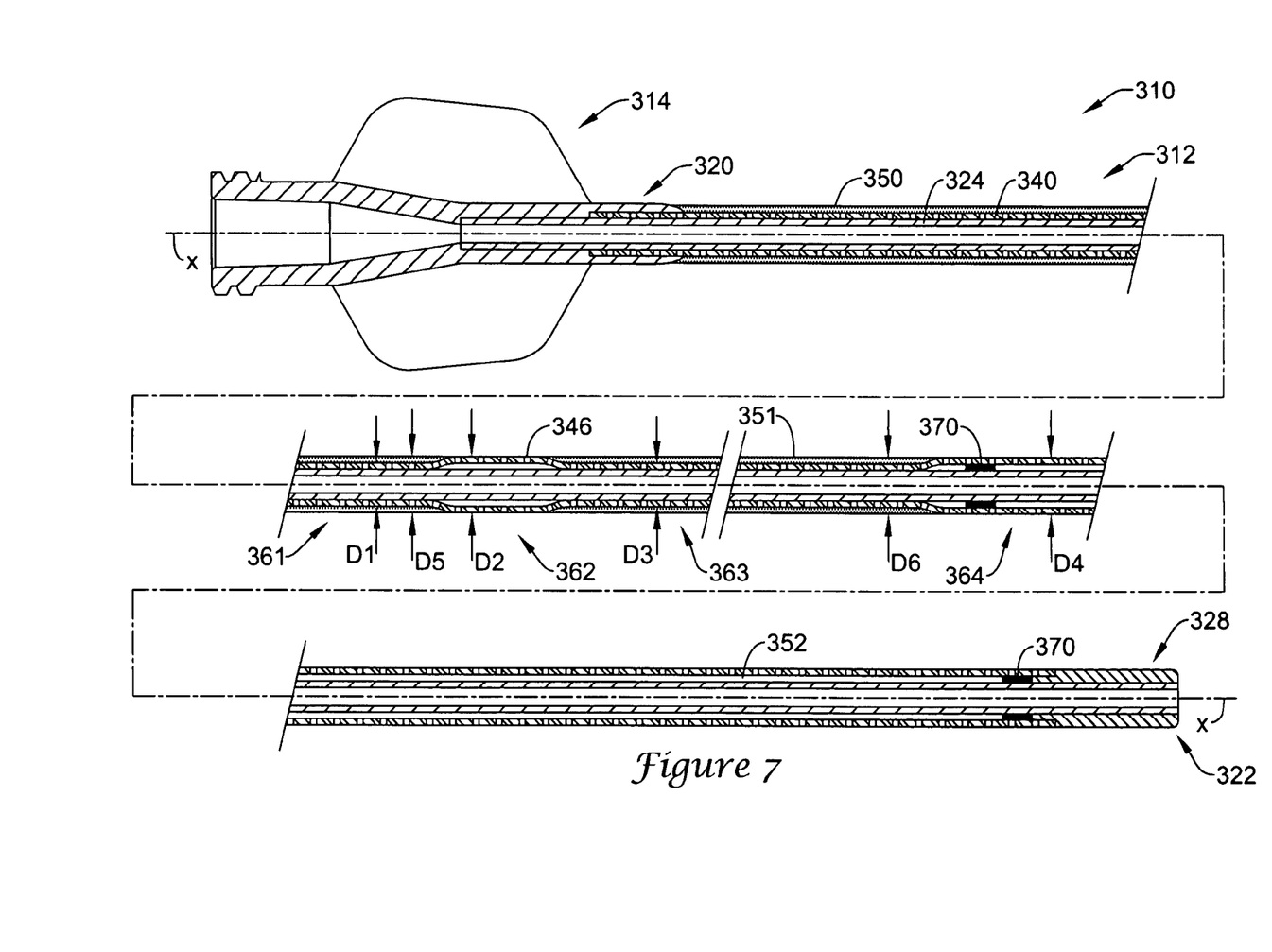
FIG. 7 is a cross-sectional view of the medical catheter of FIG. 6.

Another medical device, illustrated as a medical catheter 310 is shown in FIGS. 6 and 7. The catheter 310 includes an elongate shaft 312 extending from a proximal end 320 coupled to a manifold assembly 314 to a distal end 322 including a distal tip 328. The elongate shaft 312 includes a first region 381, a second region 382, a third region 383 and a fourth region 384. However, in other embodiments, the elongate shaft 312 may include more regions or fewer regions as desired.

The elongate shaft 312 can be manufactured, include structure, and be made of materials so as to provide the desired characteristics of the catheter 310, depending upon the intended use. For example, the elongate shaft 312 can be provided with and/or manufactured so as to maintain a desired level of flexibility, torquability and/or other characteristics appropriate for maneuvering the catheter 310 as desired, for example, through the vasculature of a patient.

The elongate shaft 312 may have a length and an outside diameter appropriate for its desired use, for example, to enable intravascular insertion and navigation. For instance, in some embodiments, the elongate shaft 312 may have a length and/or diameter similar to those expressed regarding the elongate shaft 12. The elongate shaft 312, or portions thereof, may include any suitable materials, including, but not limited to, those mentioned above regarding the elongate shaft 12. For the sake of repetitiveness, additional similarities of the elongate shaft 312 with the elongate shaft 12 will not be repeated.

Referring to FIG. 7, the elongate shaft 312 comprises a metallic tubular member 340. In many respects, the metallic tubular member 340 may be similar to the metallic tubular member 40 discussed above regarding FIG. 3A. Thus, for the sake of repetitiveness, similarities of the metallic tubular member 340 with the metallic tubular member 40 will not be repeated. For example, the metallic tubular member 340 may include a plurality of apertures 346 formed therein to provide a desired degree of flexibility to the elongate shaft 312.

The metallic tubular member 340 includes a first region 361, a second region 362 distal of the first region 361, a third region 363 distal of the second region 362, and a fourth region 364 distal of the third region 363. Each of the regions 361, 362, 363, 364 may be a generally cylindrical region. The first region 361 has an outer diameter $D_1$, the second region 362 has an outer diameter $D_2$, the third region 363 has an outer diameter $D_3$, and the fourth region 364 has an outer diameter $D_4$. In the illustrative embodiment, the outer diameter $D_2$ of the second region 362 is greater than the outer diameter $D_1$ of the first region 361 of the metallic tubular member 340. Additionally, the outer diameter $D_3$ of the third region 363 is less than the outer diameter $D_2$ of the second region 362. The outer diameter $D_4$ of the fourth region 364 is greater than the outer diameter $D_3$ of the third region 363. In some embodiments, the outer diameter $D_1$ of the first region 361 may be substantially the same as the outer diameter $D_3$ of the third region 363. Additionally or alternatively, in some embodiments, the outer diameter $D_2$ of the second region 362 may be substantially the same as the outer diameter $D_4$ of the fourth region 364. A tapered region may be located between each of the first, second, third and fourth regions 361, 362, 363, 364 to provide a transition in the outer diameter of the metallic tubular member 340 between the regions. Although the metallic tubular member 340 is illustrated as having four distinct regions of differing outer diameters, in other embodiments, the metallic tubular member 340 may include fewer or more regions of differing outer diameters along its length.

One or more of the regions 361, 362, 363, 364 of the metallic tubular member 340 may include a plurality of apertures 346 formed therein to provide a degree of flexibility to the metallic tubular member 340. However, in some embodiments, one or more of the regions 361, 362, 363, 364 may be devoid of any apertures 346 formed therein. The density of the apertures 346 in one region 361, 362, 363, 364 may be different from the density of the apertures 346 in one or more of the other regions 361, 362, 363, 364. For instance, the density of apertures 346 in the fourth region 364 may be greater than the density of apertures 346 in the first region 361, thus providing the fourth region 364 with greater lateral flexibility. In some embodiments, the density of the apertures 346 in the first region 361 may be similar to the density of the apertures 346 in the third region 363. The number, size, distribution and/or orientation of the apertures 346 may be otherwise varied along the length of the metallic tubular member 340 to impart desired flexibility properties and/or regions of the elongate shaft 312.

In some embodiments, such as the embodiment illustrated in FIG. 7, the elongate shaft 312 may also include an inner tubular member 324 disposed within the lumen of the metallic tubular member 340. The inner tubular member 324 may include and/or be made of any of a broad variety of materials and/or structures including, but not limited to, those disclosed above regarding the tubular member 24. The inner tubular member 324 may extend substantially the entire length of the elongate shaft 312, or a portion thereof. In some embodiments, such as the illustrative embodiment shown in FIG. 7, the inner tubular member 324 may have a relatively constant diameter along substantially the entire length of the inner tubular member 324. However, in other embodiments, the diameter of the inner tubular member 324 may vary in and/or along different regions of the catheter 310.

In some embodiments, such as the embodiment illustrated in FIG. 7, the inner tubular member 324 may be spaced away from the inner surface of the metallic tubular member 340, forming a space or gap 352 therebetween. Thus, in some embodiments the inner tubular member 324 may be coaxially disposed within and spaced from the metallic tubular member 340, creating an annular gap 352 therebetween.

The inner tubular member 324 may be coupled to the metallic tubular member 340 at one or a plurality of discrete attachment points 370 throughout the length of the metallic tubular member 340. For example, in some embodiments the inner tubular member 324 may be coupled to the proximal end of the metallic tubular member 340, the distal end of the metallic tubular member 340, and/or at one or more intermediate locations of the metallic tubular member 340 at a discrete attachment point 370. In some embodiments, such attachment points 370 can be achieved, for example, using an adhesive material, for example, a cyanoacrylate, or other suitable type of adhesive. In at least some embodiments, only a relatively small portion of the metallic tubular member 340 is connected to the inner tubular member 324 at the attachment points 370. For example, the length of each individual bond joint, especially at intermediate bond joints, may only be about 5 cm or less, or 3 cm or less, or 1 cm or less, or 0.5 cm or less.

The inner tubular member 324 may extend proximal and/or distal of the metallic tubular member 340 in order to facilitate securement of the elongate shaft 312 to the manifold assembly 314 and/or the distal tip 328, respectively. For instance, a proximal portion of the inner tubular member 324 may extend proximal of the proximal end of the metallic tubular member 340 such that the proximal portion may be bonded or otherwise secured to the manifold assembly 314, using conventional techniques. Additionally or alternatively, a distal portion of the inner tubular member 324 may extend distal of the distal end of the metallic tubular member 340 such that the distal tip 328 may be formed with or otherwise include a distal portion of the inner tubular member 324.

In the illustrative embodiment, the elongate shaft 312 further includes a first polymeric member 350 extending over at least a portion of the first region 361, which may be referred to as a reduced diameter region, of the metallic tubular member 340. In many respects, the first polymeric member 350 may be similar to the polymeric member 50, thus for the sake of repetitiveness, similarities of the polymeric member 350 with the polymeric member 50, such as suitable materials and/or dimensions, will not be repeated.

As shown in FIG. 7, the first polymeric member 350 may extend over the first region 361 of the metallic tubular remember 340 from the manifold assembly 314 to the tapered region proximate the second region 362 of the metallic tubular member 340. However, in other embodiments, the first polymeric member 350 may extend from the tapered region proximate the second region 362 to a point proximate the proximal end of the metallic tubular member 340, thus may extend within the manifold assembly 314. The first polymeric member 350 has an outer diameter $D_5$. In the illustrative embodiment, the outer diameter $D_5$ of the first polymeric member 350 is substantially equivalent to the outer diameter $D_2$ of the second region 362 of the metallic tubular member 340, thus forming a uniform transition along the elongate shaft 312. However in other embodiments, the outer diameter $D_5$ of the first polymeric member 350 and the outer diameter $D_2$ of the second region 362 of the metallic tubular member 340 may be dissimilar, thus creating a transition in the outer diameter of the elongate shaft 312 at the transition between the first polymeric member 350 and the metallic tubular member 340.

In some embodiments, the first polymeric member 350 may be extruded over the metallic tubular member 340, the first polymeric member 350 may be molded onto the metallic tubular member 340, or the first polymeric member 350 may be heat shrunk onto the metallic tubular member 340. In other embodiments, the first polymeric member 350 may be positioned over a portion of the metallic tubular member 340 in other fashions known in the art.

In the illustrative embodiment, the elongate shaft 312 further includes a second polymeric member 351 extending over at least a portion of the third region 363, which may be referred to as a reduced diameter region, of the metallic tubular member 340. In many respects, the second polymeric member 351 may be similar to the polymeric member 50, thus for the sake of repetitiveness, similarities of the polymeric member 351 with the polymeric member 50, such as suitable materials and/or dimensions, will not be repeated.

As shown in FIG. 7, the second polymeric member 351 may extend over the third region 363 of the metallic tubular member 340 from the tapered region proximate the second region 362 to the tapered region proximate the fourth region 364 of the metallic tubular member 340. Thus, the second polymeric member 351 may overlay substantially the entire third region 363. However, in other embodiments, the second polymeric member 351 may extend over any portion of the third region 363 as desired. The second polymeric member 351 has an outer diameter $D_6$. In the illustrative embodiment, the outer diameter $D_6$ of the second polymeric member 351 is substantially equivalent to the outer diameter $D_2$ of the second region 362 of the metallic tubular member 340 and the outer diameter $D_4$ the fourth region 364 of the metallic tubular member, thus forming a uniform transition along the elongate shaft 312. However in other embodiments, the outer diameter $D_6$ of the second polymeric member 351 and the outer diameter $D_2$ of the second region 362 and/or the outer diameter $D_4$ of the fourth region 364 of the metallic tubular member 340 may be dissimilar, thus creating a transition in the outer diameter of the elongate shaft 312 at the transition between the second polymeric member 351 and the metallic tubular member 340.

In some embodiments, the second polymeric member 351 may be extruded over the metallic tubular member 340, the second polymeric member 351 may be molded onto the metallic tubular member 340, or the second polymeric member 351 may be heat shrunk onto the metallic tubular member 340. In other embodiments, the second polymeric member 351 may be positioned over a portion of the metallic tubular member 340 in other fashions known in the art.

Referring again to FIG. 6, it can be seen that in the illustrative embodiment, the metallic tubular member 340 is exposed in the second region 382 of the elongate shaft 312 intermediate the first polymeric member 350 and the second polymeric member 351. The second region 362 of the metallic tubular member 340 corresponding to the second region 382 of the elongate shaft 312 includes a plurality of apertures 346 formed therein to provide a desired lateral flexibility to the second region 382 of the elongate shaft 312. Thus, the second region 382 of the elongate shaft 312 may define a flexible joint or elbow 390 providing the elongate shaft 312 with a desired degree of flexibility at least in this region. In some embodiments, the second region 382 of the elongate shaft 312 may be constructed such that the second region 382 has a greater flexibility than either the first region 381 and/or the third region 383.

Additionally, as shown in FIG. 6, the metallic tubular member 340 is exposed in the fourth region 384. The fourth region 364 of the metallic tubular member 340 corresponding to the fourth region 384 of the elongate shaft 312 includes a plurality of apertures 346 formed therein to provide desired lateral flexibility to the fourth region 384 of the elongate shaft 312. Thus, the fourth region 384, which may be the most distal region of the elongate shaft 312, may have a high degree of lateral flexibility in order to navigate a tortuous anatomy, such as the vasculature of a patient.

The medical devices described herein can be partially or completely coated with a lubricious or other type of coating. Hydrophobic coatings such as fluoropolymers provide a dry lubricity that can improve handling and device exchanges. An example of a suitable fluoropolymer is polytetrafluoroethylene (PTFE), commonly known as TEFLON®.

Lubricious coatings can improve steerability and improve lesion crossing capability of the medical device. Examples of suitable lubricious polymers include hydrophilic polymers such as polyarylene oxides, polyvinylpyrolidones, polyvinylalcohols, hydroxyl alkyl cellulosics, algins, saccharides, caprolactones, and the like, and mixtures and combinations thereof. Hydrophilic polymers can be blended among themselves or with formulated amounts of water insoluble compounds (including some polymers) to yield coatings with suitable lubricity, bonding, and solubility. In some embodiments, a distal portion of a medical device can be coated with a hydrophilic polymer as discussed above, while a more proximal portion can be coated with a fluoropolymer or other hydrophobic coating.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A medical catheter comprising:
   a manifold assembly including a bore extending therethrough, the bore of the manifold assembly in fluid communication with a lumen of the medical catheter; and
   an elongate shaft extending distally from the manifold assembly, the elongate shaft including:
      a metallic tubular member extending distally from the manifold assembly, the metallic tubular member formed of a monolithic tubular body including a plurality of annular ring portions interconnected by a plurality of beams extending transverse to the annular ring portions by the removal of material of the tubular body between adjacent annular rings to form a plurality of apertures therein to provide a desired degree of lateral flexibility to the metallic tubular member, the metallic tubular member including a proximal region having an outer diameter, a distal region having an outer diameter different from the outer diameter of the proximal region wherein the outer diameter of the distal region is greater than the outer diameter of the proximal region, and a tapered region intermediate the proximal region and the distal region to provide a transition between the outer diameter of the proximal region and the outer diameter of the distal region; and
      a polymeric distal tip extending distally from the metallic tubular member to a distal end of the medical catheter;
      wherein the lumen of the medical catheter extends through the polymeric distal tip to the distal end of the medical catheter; and
      wherein a proximal portion of the metallic tubular member extends into the bore of the manifold assembly.

2. The medical catheter of claim 1, wherein the elongate shaft further includes a polymeric member extending over at least a portion of the proximal region of the metallic tubular member.

3. The medical catheter of claim 2, wherein the polymeric member extends from the manifold assembly to the tapered region of the metallic tubular member.

4. The medical catheter of claim 3, wherein the polymeric member has an outer diameter substantially the same as the outer diameter of the distal region of the metallic tubular member.

5. The medical catheter of claim 1, wherein the elongate shaft further includes an inner tubular member disposed in a lumen of the metallic tubular member.

6. The medical catheter of claim 5, wherein the inner tubular member is spaced away from the distal region of the metallic tubular member, defining a gap between an outer surface of the inner tubular member and an inner surface of the distal region of the metallic tubular member.

7. The medical catheter of claim 1, wherein apertures in the distal region of the metallic tubular member are exposed to the exterior of the medical catheter.

8. A medical catheter comprising:
   a manifold assembly including a bore in fluid communication with a lumen of the medical catheter;
   a metallic tubular member having a proximal end, a distal end, and a lumen extending therethrough, wherein the metallic tubular member is formed of a monolithic tubular body including a plurality of annular ring portions interconnected by a plurality of beams extending transverse to the annular ring portions by the removal of material of the tubular body between adjacent annular rings to form a plurality of apertures therein to provide a desired degree of flexibility to the metallic tubular member, the metallic tubular member including a distal region and a more proximal reduced diameter region relative to the distal region;
   a polymeric material extending over at least a portion of the proximal reduced diameter region of the metallic tubular member; and
   a polymeric distal tip extending distally from the metallic tubular member to a distal end of the medical catheter;
   wherein the lumen of the medical catheter extends through the polymeric distal tip to the distal end of the medical catheter; and
   wherein the proximal end of the metallic tubular member is located within the bore of the manifold assembly.

9. The medical catheter of claim 8, further comprising a tapered region intermediate the proximal reduced diameter region and the distal region.

10. The medical catheter of claim 8, further comprising an inner tubular member disposed in the lumen of the metallic tubular member.

11. The medical catheter of claim 9, wherein the proximal reduced diameter region of the metallic tubular member includes a first density of apertures formed therein, and the distal region of the metallic tubular member includes a second density of apertures formed therein different from the first density of apertures.

12. The medical catheter of claim 11, wherein the first density of apertures is greater than the second density of apertures.

13. The medical catheter of claim 11, wherein the first density of apertures is less than the second density of apertures.

14. The medical catheter of claim 8, wherein the polymeric material has an outer diameter and the distal region of the metallic tubular member has an outer diameter, wherein the outer diameter of the polymeric material is substantially the same as the outer diameter of the distal region of the metallic tubular member.

15. A medical catheter comprising:
a manifold assembly including a bore extending therein from a proximal end to a distal end of the manifold assembly, the bore of the manifold assembly in fluid communication with a lumen of the medical catheter; and
an elongate shaft coupled to the manifold assembly and extending distally therefrom, wherein the elongate shaft comprises:
a metallic tubular member having a proximal end, a distal end, and a lumen extending therethrough, the metallic tubular member including a proximal portion having a first outer diameter extending distally from the proximal end and a distal portion having a second outer diameter greater than the first outer diameter of the proximal portion wherein the metallic tubular member is formed of a monolithic tubular body including a plurality of annular ring portions interconnected by a plurality of beams extending transverse to the annular ring portions by the removal of material of the tubular body between adjacent annular rings to form a plurality of apertures therein to provide a desired degree of flexibility of the metallic tubular member; and
a polymeric distal tip extending distally from the metallic tubular member to a distal end of the medical catheter;
wherein the lumen of the medical catheter extends through the polymeric distal tip to the distal end of the medical catheter; and
wherein at least a portion of the proximal portion of the metallic tubular member having the first outer diameter extends into the bore of the manifold assembly.

16. The medical catheter of claim 15, wherein the elongate shaft further includes a polymeric material extending over at least a portion of the proximal portion of the metallic tubular member.

17. The medical catheter of claim 16, wherein the polymeric material extends from the manifold assembly to the distal portion.

18. The medical catheter of claim 15, wherein the elongate shaft further includes an inner tubular member extending through at least a portion of the lumen of metallic tubular member.

19. The medical catheter of claim 18, wherein the inner tubular member is spaced away from the distal portion of the metallic tubular member, defining a gap between an outer surface of the inner tubular member and an inner surface of the distal portion of the metallic tubular member.

20. The medical device of claim 15, wherein a portion of the polymeric distal tip overlaps a portion of the metallic tubular member.

21. The medical device of claim 15, wherein the elongate shaft further includes an inner tubular member extending through at least a portion of the lumen of the metallic tubular member.

22. The medical device of claim 21, wherein the polymeric distal tip is disposed around a distal portion of the inner tubular member.

23. The medical device of claim 22, wherein the polymeric distal tip is disposed around the distal end of the metallic tubular member.

* * * * *